United States Patent [19]

Kaplan

[11] Patent Number: 5,045,316

[45] Date of Patent: Sep. 3, 1991

[54] PHARMACEUTICAL COMPOSITIONS AND THEIR USE

[76] Inventor: Ephraim Kaplan, 5 Barnizki Street, Rishon Lezion, Israel

[21] Appl. No.: 136,100

[22] Filed: Dec. 21, 1987

[30] Foreign Application Priority Data

Jan. 5, 1987 [IL] Israel ........................................ 81166

[51] Int. Cl.$^5$ ......................... A61K 9/00; A01N 59/00
[52] U.S. Cl. .................................... 424/400; 424/422; 424/436; 424/600; 424/465; 424/451; 424/489; 424/712; 514/553; 514/824
[58] Field of Search ............... 424/400, 422, 436, 702, 424/600, 451, 489, 465; 514/824, 553

[56] References Cited

U.S. PATENT DOCUMENTS

| | | | |
|---|---|---|---|
| 2,135,111 | 11/1938 | Prebluda | 424/131 |
| 4,462,988 | 7/1984 | Alvarez | 424/162 |
| 4,464,357 | 8/1984 | Alvarez | 424/162 |
| 4,532,131 | 7/1985 | Alvarez | 424/162 |
| 4,657,764 | 4/1987 | Alvarez | 424/162 |

FOREIGN PATENT DOCUMENTS 3419686 5/1984 Fed. Rep. of Germany .

OTHER PUBLICATIONS

Chemical Abstracts, vol. 57, p. 3979, Paragraph A., G. M. Kosolapoff.
"Studies on the Antineoplastic Effect of Vanadium Salts" Jorgen Kieler, Andrezej Gromek and Nis. I. Nisen, pp. 154–164.
Henry J. Thompson. N. Dennis Chasteen, and L. David Mecker, "Dietary Vanadyl (IV) Sulfate Inhibits Chemically–Induced Mammary Carcinogenisis" Carcinogenisis, vol. 5, No. 6, pp. 849–851, 1984.
Chemical Abstracts, vol. 57, pp. 3979–3980.
Chemical Abstracts, vol. 102, pp. 56148, 86.

*Primary Examiner*—Josephine Barr
*Attorney, Agent, or Firm*—Helfgott & Karas

[57] ABSTRACT

Pharmaceutically active combination comprising an ionic vanadium compound and thiosulphate or sulfite compound and optionally selenium, pharamceutical compositions containing same and method for treating malignant tumors, arteriosclerosis and mental syndromes in the elderly.

19 Claims, No Drawings

PHARMACEUTICAL COMPOSITIONS AND THEIR USE

The present invention concerns pharmaceutical compositions for the prevention and treatment of various pathological conditions.

BACKGROUND OF THE INVENTION

Vanadium compounds which contain the VO radical, have rarely been used in pharazcology. U.S. Pat. No. 2,135,11 suggests that vanadyl lactate and possibly other vanadyl carboxylates have anti-septic and in particular insecticidal and fungicidal properties Jorgen Kieler et al, *Acta Chir.Scan Suppl* ,1965,343, 154 reported on the antineoplastic effect of vanadium salts in mice and suggested that vanadium compounds might be of value in the treatment of neoplasia Henry J. Thompson et al—*Carcinogenesis*, Vol. 5, No. 6, pp. 849-851, 1984—reported that dietary vanadyl (IV) sulfate inhibits chemically-induced mammary carcinogenesis in rats.

These disclosures do not appear to have led to the use of vanadium compounds for the stated purposes Sulfur and its derivatives, on the other hand, have a long history of pharmaceutical utility. Thus for example, besides the sulfa drugs and sulfur itself, thiosulphates find pharmacological applications in the treatment of cyanide poisoning, allergic conditions and drug sensitization caused by gold, arsenic, mercury or bismuth preparations. Magnesium thiosulphate tablets and injectable aqueous solutions are marketed for treatment of shock, medicaxent intolerance and anaphylactic conditions due to serums or vaccines among other things Sulfite compounds also display some pharmacological activity such as against certain parasitic and infectious conditions. Recently, German patent publication No. 3,419,686 disclosed sulfite or bisulfite solutions for treating arthritis or epilepsy, and PCT Int. Appl. WO 84 02,527 claims increased antitumour activity for adriamycin and daunomycin with the addition of sulfites, acid sulfites, pyrosulfites, dithionites and/or anhydrous sulfites.

The applicant has surprisingly found that the combination of ionic vanadium with a thiosulphate or sulfite is effective for the treatment and often prevention of a variety of pathological conditions, to an extent not possible before. This combination is effective against some conditions quite different from those for which vanadium, thiosulphates, or sulfites alone have been proposed.

SUMMARY OF THE INVENTION

The present invention accordingly provides novel compositions comprising a combination of an ionic vanadium compound and a thiosulphate or a sulfite compound.

The invention further comprises a pharmaceutical composition containing the above compounds as active ingredients, together with an inert carrier diluent or excipient.

Another object of the invention is to provide a process for preparing such compositions and methods for using them.

The compositions of the invention are particularly useful for the treatment or prevention of such diverse conditions as arterio-sclerosis, malignant tumours in mammals and mental syndromes in the elderly.

DETAILED DESCRIPTION OF THE INVENTION

The compositions of this invention may include any ionic vanadium compound but preferably vanadyl or vanadate salts. Water soluble salts are preferred and particularly the vanadium salts of non-toxic, organic or inorganic acids and bases such as vanadyl lactate, vanadyl tartrate, vanadyl citrate and vanadyl sugar-derived carboxylate such as vanadyl gluconate, vanadyl phosphate and sodium vanadate, to mention just a few.

The thiosulphate and sulfite compounds can be selected from alkali and alkali earth metal salts such as lithium, sodium, potassium, calcium and magnesium salts, the magnesium thiosulphate being the preferred thiosulphate compound. Sodium sulfite is the preferred sulfite compound. Organic sulfites can also be used We have also found that when sulfite is used in the inventive composition, further addition of some selenium may provide increased benefit In the compositions of the present invention, the thiosulphate comprises from about 100 to about 20,000 parts per part of vanadium compound and the sulfite comprises from about 100 to 10,000 parts for each part of vanadium compound. When selenium is incorporated in the composition, it is present in about the same range as the vanadium compound The compositions can be prepared in the known manner for blending and mixing pharmaceutically active compositions. Thus the compounds may be mixed as dry components or they may be mixed in the presence of solvent, followed by removal of the solvent. It will be appreciated that thiosulphates and sulfites are pH sensitive and therefore it is preferable to avoid alkaline or acidic conditions which may effect the thiosulphate or sulfite. It is therefore desirable to neutralize the vanadium compound to a pH of about 6.5 to about 7.5 prior to its being mixed with the thiosulphate or sulfite component. Any suitable non-toxic agent may be used for the neutralization step, as for example sodium bicarbonate, magnesium oxide and magnesium hydroxicarbonate. Similarly the sulfite may be neutralized before mixing it with the vanadium compound with a suitable non-toxic weak acid, such as acetic acid.

Following the neutralization step of the vanadium compound, it is desirable to remove any insoluble matter to clarify the solution before proceeding further.

Thus the neutralized vanadium compound solution having a pH of about 6.5 to about 7.5 is filtered to remove insoluble matter and then evaporated under an inert gas ataosphere. The residue can be maintained for any desired period of time. The vanadium compound residue can then subsequently be mixed with an aqueous solution of thiosulphate or sulfite. If desired, this final solution may also be evaporated to dryness, providing a solid mixture of the composition.

The composition prepared as above can of course be formulated with any known carrier, diluent or excipient as is the practice in the pharmaceutical industry. It should be understood however that the invention includes compositions containing only the active ingredients in the absence of such ajuvents. Such concentrate compositions may be administered as such but more generally will be used as master batches to make up required dosages with suitable carriers, diluents or excipients.

The pharmaceutical compositions of the present invention may be provided in a form suitable for oral, perinteral, rectal or topical administration, and may be in unit dosage form. The compositions may be in the form of tablets, capsules, powders, syrups, suspensions, orally. administerable solutions, injectable solutions, particularly solutions suitable for intra-muscular or intra-venous injection, including especially aqueous solutions, ointments, suppositories or any other pharmaceutically acceptable form.

The compositions of the invention, comprising an ionic vanadium compound and a thiosulphate compound, are useful for treating arterio-sclerosis or malignant tumours in mammals, as well as mental syndromes in the elderly. The compositions comprising ionic vanadium compounds and sulfite compounds, and optionally selenium, are useful for treating malignant tumours in mammals. The term mammals is intended to mean both humans and non-human mammals, such as horses and cattle. The amounts of active components in the dosages used to treat the foregoing conditions will normally be such as to provide a daily dosage from about 0.3 to about 18.0 mg vanadium as vanadyl compound and from about 0.2 to 5.0 grm thiosulphate or 0.2 to 1.0 grm sulfite, when administered by injection. Owing to the lower absorption of vanadium when administered orally, the quantity of vanadium as vandyl when administered orally can be considerably increased, e.g. up to about 40 mg and the quantity of thiosulphate can be correspondingly increased, e.g. up to about 10.0 grm and that of sulfite to about 5.0 grm. These doses are of course variable depending on the form in which the medication is administered. Such quantities of the active compounds may be conveniently adxinistered in the form of 1–6 unit dosages daily. In vanadium-sulfite-selenium compositions, the selenium is present in about the same range as the vanadium compound.

It is presently believed that the compositions of the invention are effective in preventing or delaying the incidence of the pathological condition mentioned above. This belief is supported by preliminary clinical studies carried out by the inventor However, it will be appreciated by those skilled in the art that it is considerably more difficult to establish prevention of a disease or condition which has not yet occurred, than it is to show that an existing disease or condition has been cured, or at least ameliorated, by treatment.

As is known, the quantities of therapeutic agents useful for prevention are usually a fraction of the quantities useful for treating a condition. It is presently believed that the amounts of the active components in the compositions of the invention which will be useful to prevent the foregoing conditions will normally be such as to provide a daily dosage of from about 0.06 to about 9.0 mg vanadium as vanadyl compound and from about 0.04 to about 2.5 grm thiosulphate or 0.04 to about 0.5 grm sulfite and optionally 0.06 mg to about 9.0 mg selenium, when administration is by injection. Owing to the lower absorption of vanadyl compound when administered orally, the quantity of vanadium as vanadyl administered by the oral route can be considerably increased, e g. up to about 13.3 mg and the quantity of thiosulphate can be correspondingly increased, e.g. up to about 3.3 grm and that of sulfite to about 1.0 grm and that of selenium to about 18.0 mg. It will be apparent to those skilled in the art how the quantities of active ingredients are adjusted when other forms of administration are used As with the compositions of the invention to be used for treatment, such quantities of the active compounds may conveniently be administered in the form of 1 to 6 unit dosages daily.

It will be appreciated by those skilled in the art that the actual daily dosages of the compositions of the invention to be administered to a patient or to a non-human mammal will lie entirely within the discretion of the physician or veterinarian, as the case may be. Whether the daily dosage for treatment of a condition, or prevention of a condition, will lie within the ranges of quantities stated above, or whether the daily dosage will be above or below such ranges, will depend on such factors as the sex and maturity of the patient or non-human mammal, its weight, and where treatment especially is concerned, the nature and severity of the condition itself.

It will be evident, for example, that taking the ranges of quantities described above as generally including typical daily dosages for an adult human male of average weight (i.e. about 70 kg), an adult female or child (or for that matter a non-human mammal of lesser weight than the average human male) is, other factors being equal, likely to require a daily dosage of the active components in the lower part of these ranges, or below the minima of one or both of these ranges, whereas the converse would be expected when dealing with e.g. either humans or non-human mammals which are heavier than the average human male.

Moreover, it will be evident to those skilled in the art that administering these two components separately would in a sense be an obvious equivalent of administering these components as part of the same composition. Nevertheless, besides the convenience of using a single type of dosage unit comprising both active components, it is believed that such separate administration is likely to be relatively inferior. Thus, while the present invention is not to be restricted by any theory of the manner in which the components act in the body, it is possible that one component acts to promote the activity of the other component, or perhaps that the two components act synergistically.

Any such manner of cooperative action would require the two components to be present in the optimum concentration together, whereas a time lag between the administration of the components is likely to act so as to minimize the possibility that such optimum concentration would be obtained and to require higher doses of the active ingredients, which undesirably approach the toxic limits.

The invention will now be illustrated by the following non-limitative Examples. In all cases the vanadyl gluconate solutions were obtained by reacting together vanadyl sulphate and calcium gluconate solutions, removing the thus-formed calcium sulphate by filtration or centrifugation, and recovering the filtrate or supernate containing vanadyl gluconate. The presence of negligible quantities of calcium sulphate and/or glutonate in the filtrate or supernate does not adversely affect the compositions of the invention. The neutralization step is effected using sodium bicarbonate, magnesium oxide or magnesium hydroxycarbonate, followed if necessary by clarification by filtration or centrifugation. The presence of small quantities of sodium or magnesium ions in the thus-obtained filtrate or supernate does not adversely affect the compositions of the invention. The sulfite used in the Examples was sodium sulfite neutralized with acetic acid.

EXAMPLE 1

Daily injections of 10 ml 12% magnesium thiosulphate aqueous solution, to which had been added neutralized vanadyl gluconate aqueous solution containing 1.5 mg vanadium as vanadyl radical, were administered to 10 patients suffering from various forms of arteriosclerosis. In all cases there was observed a marked and steady improvement in their clinical condition after 1-3 months of treatment. The injections were given intramuscularly in 8 cases and intravenously in 2 cases. No side effects were observed.

EXAMPLE 2

Daily intramuscular injections of 10 ml 12% magnesium thiosulphate aqueous solution, to which had been added neutralized vanadyl gluconate aqueous solution containing 3.0 mg vanadium as vanadyl radical, were administered to 7 patients suffering from various forms of malignant tumours (1 breast tumour, 3 prostate tumours, 1 multiple myeloma and 2 bladder tumours, in different patients). All the patients were regarded as terminal or pre-terminal, and previous treatments were non-beneficial. There was observed a marked improvement in all cases after 2-3 weeks of treatment. Complete clinical recovery was observed in 4 cases after 4 months. No side effects were observed

EXAMPLE 3

Daily intramuscular injections of 10 ml 12% magnesium thiosulphate aqueous solution, to which had been added neutralized vanadyl gluconate aqueous solution containing 5.0 mg vanadium as vanadyl radical, were administered to 10 elderly patients suffering from organic geriatric mental syndromes. After one month of treatment, there was observed a marked improvement in 7 cases and a slight improvement in 3 cases. No side effects were observed.

EXAMPLE 4

Daily intramuscular injections of 10 ml of 3% neutralized sodium sulfite aqueous solution, to which had been added neutralized vanadyl gluconate aqueous solution containing 3.0 mg vanadium as vanadyl radical, were administered to two patients suffering from various forms of malignant tumours (1 lung tumour and 1 large intestine tumour with liver methasthastes). The patients were regarded as terminal or pre-terminal, and previous treatments with conventional medication were non-beneficial. There was observed a marked improvement in the cases after 2-3 weeks of treatment. Complete clinical recovery was observed after 4 months. No side effects were observed

EXAMPLE 5

Two male patients, one 79-years old and the other 84-years old, both with proven prostate cancer, were treated for four months with daily injections comprising a 10 cc. solution containing 1.2 grms magnesium thiosulmhate and 3 mgs vanadiaum as vanadyl gluconate. Both patients were completely cured of the cancer and have remained cured until now, three years later. In both cases, conventional chemotherapeutic treatments failed.

Two other patients, however, with terminal cases of proven prostatic cancer, were treated in the same way but the treatment did not provide any improvement.

EXAMPLE 6

A woman who had been operated for a Duke C adenocarcinoma of the colon subsequently developed a trans-vaginal metastasis that was continually growing and bleeding and was inoperable and untreatable by radiation therapy. The woman was treated, as in the previous example, with daily injections of a 10 cc solution containing 1.2 grms magnesium thiosulphate and 3 mgs vanadium as vanadyl gluconate, plus local treatment (vaginal suppositories) After two months the tumour was stabilized, bleeding ended and it became mobile and operable.

The woman is still alive today, 18 months after treatment.

EXAMPLE 7

A male patient aged 80, suffering from a terminal case of multiple myeloma, had a dramatic remission during four months of treatment as above and became almost normally active. On the other hand, a woman patient with a terminal case of ovary cancer with peritoneal seeding and ascites, did not recover after treatment with daily injections of a 10 cc solution containing 1.2 grms magnesium thiosulphate and 3 mgs vanadium as vanadyl gluconate, although there was some improvement after one month of treatment.

EXAMPLE 8

A male patient aged 74, suffering from a pre-terminal case of colon adenocarcinoma with liver and lymph nodes metastasis, was treated three times a week with 10 cc IM injections of a solution containing 750 mgs sodium sulphite and 3 mgs vanadium as vanadyl gluconate. The patient lived for seven months after treatment began Another patient, a 67-year old man having a very similar condition, was treated for six weeks in the same way and then decided to stop the treatment. He died two weeks after treatment stopped.

EXAMPLE 9

A 61-year old woman patient, with a very rapidly progressing cancer at the head of the pancreas which was beyond any conventional treatment, was subjected for two months to daily injections of a 15 cc solution containing 10% sodium sulphite, 3mgs vanadium as vanadyl gluconate and 2 mgs of selenium as sodium selenite. The woman was completely cured and curation was verified by CT scan and ultra-sound. A check on her condition after seven months showed the cure to be still in effect.

EXAMPLE 10

A 74-year old man, having an inoperable stomach adenocarcinoma, was treated with daily injections of a 30 ml. solution containing 15% sodium sulphite plus 3 mgs vanadium as vanadyl gluconate and 2 mgs of seleniun as sodium selenite for one month and subsequently with a similar solution wherein sodium vanadate was substituted for vanadium gluconate. The patient was completely cured, as verified by CT scan. A gastroscopy is pending.

EXAMPLE 11

Two patients, having pulmonary cancer of metastetic origin (colon adenocarcinoma), failed to respond to conventional treatment. After three months of treatment with 20-30 ml injections of solutions containing 10-15% sodium sulphite and 3 mgs vanadium as sodium vanadate, their condition was improved and radiologically stabilized or improved.

EXAMPLE 12

Two patients suffering from primitive pulmonary cancers, which were inoperable and were non-responsive to conventional chemotherapy, were treated for three months in the same manner as in Example 11. Both patients were ameliorated and radiologically stabilized One of them had bone metastesis, which disappeared, as verified by a bone scan.

EXAMPLE 13

A patient suffering from untreatable liver cancer (metastatic) improved and is still alive after five months of treatment with daily injections as in Example 11. The liver lesions were stabilized.

On the other hand, five other cases of advanced liver cancer did not respond to such treatment. This would indicate that the combination of this invention does not work well on advanced liver cancer patients.

EXAMPLE 14

A woman patient aged 39, after sub-total gastrectomy, developed adenocarcinoma of the stomach. She also had a liver metastesis on the right lobe. After two months of treatment with daily injections of a 20 ml solution containing 10% sodium sulphite and 3 mgs vanadium as sodium vanadate plus 2 mgs selenium as sodium selenite, the liver metastesis disappeared, as verified by ultra-sound. The woman is still under treatment and alive after 4 months.

EXAMPLE 15

A female boxer dog, weighing 26 kgs, having mammary adenocarcinoma, was treated with daily injections of a 15 am solution of 15% sodium sulphite and 1.5 mgs vanadium as vanadyl gluconate plus 1 mg selenium as sodium selenite. A shrinking of more than three quarters of the tumour occurred after one month of treatment. When the remaining tumour was excised, serial biopsis showed the disappearance of most of the tumour with no harm to the normal structures of the gland.

I claim:

1. A pharmaceutically active combination comprising an ionic vanadium compound selected from the group consisting of vanadyl salts of non-toxic organic and inorganic acids and vanadate salts and a sulfur containing compound selected from the group consisting of thiosulfate compounds and sulfite compounds, said combination being in the ratio of
vanadium compound to thiosulfate compound from about 1:4.5 to about 1:40,000, and
vanadium compound to sulfite compound from about 1:4.5 to about 1:10,000.

2. A pharmaceutically active combination as in claim 1, comprising an ionic vanadium compound and a thisoulphate containing compound.

3. A pharmaceutically active combination as in claim 1, comprising an ionic vanadium compound and a sulfite containing compound.

4. A combination as in claim 3, wherein the sulfite containing compound is in the form of an alkali or alkali earth metal salt.

5. A combination as in claim 2, wherein the ratio of vanadium compound to the thiosulphate containing compound if rom 1:100 to about 1:20,000.

6. A combination as in claim 1, wherein the ratio of vanadium compound to the sulfite containing compound is from 1:100 to about 1:10,000.

7. A combination as in claim 3 comprising an ionic vanadium compound and a sulfite containing compound with additional amounts of selenium wherein the ratio of vanadium compound, sulfite compound and selenium is from 1:100:1 to 1:10,000:1.

8. A combination as in claim 1, wherein the vanadium is selected from vanadyl lactate, vanadyl tartrate, vanadyl citrate, vanadyl gluconate and sodium vanadate.

9. A combination as in claim 8, wherein the ionic vanadium compound is vanadyl gluconate.

10. A combination as in claim 1, wherein the thiosulphate containing compound and the sulfite containing compound are in the form of their alakli or alakline earth metal salts.

11. A combination as in claim 10 wherein the alkali and alkaline earth metal salts are selected from the salts of lithium, sodium, potassium, calcium and magnesium.

12. A combination as in claim 1, wherein the sulfite containing compound is an organic sulfite containing compound.

13. A pharamceutical composition comprising the active combination as claimed in claim 1 toether with a pharamceutical acceptable carrier, diluent or excipient.

14. A pharmaceutical composition as in claim 13 containing one or more dosage units, each dosage unit comprising from about 0.06 mg to 18.0 mg vanadium compound and about 0.04 grm to 5.0 grm thiosulphate.

15. A pharmaceutical composition as in claim 13 containing one or more dosage units, each dosage unit comprising from about 0.06 mg to 18.0 mg vanadium compound and about 0.05 grm to 1.0 grm sulfite containing compound.

16. A pharmaceutical composition as in claim 15 comprising in addition 0.06 mg to 18.0 mg selenium.

17. A method for treating malignant tumours in mammals, which comprises administering to said mammals a composition according to claim 13.

18. A method for treating arteriosclerosis in mammals, which comprises administering to said mammals a composition according to claim 13.

19. A method for treating mental syndromes in the elderly, which comprises administering a composition according to claim 13.

* * * * *